(12) United States Patent
Espinosa

(10) Patent No.: US 12,178,391 B2
(45) Date of Patent: Dec. 31, 2024

(54) ENDOSCOPY DEVICE HAVING AN ELECTRICAL CONTROL SYSTEM

(71) Applicant: EvoEndo, Inc., Centennial, CO (US)

(72) Inventor: Alejandro Espinosa, Miami, FL (US)

(73) Assignee: EVOENDO, INC., Centennial, CO (US)

( * ) Notice: Subject to any disclaimer, the term of this patent is extended or adjusted under 35 U.S.C. 154(b) by 0 days.

(21) Appl. No.: 18/108,564

(22) Filed: Feb. 10, 2023

(65) Prior Publication Data

US 2024/0268631 A1  Aug. 15, 2024

(51) Int. Cl.

| | |
|---|---|
| A61B 1/00 | (2006.01) |
| A61B 1/018 | (2006.01) |
| A61B 1/045 | (2006.01) |
| A61B 1/05 | (2006.01) |
| A61B 1/06 | (2006.01) |
| A61B 1/233 | (2006.01) |

(52) U.S. Cl.
CPC ........ *A61B 1/00096* (2013.01); *A61B 1/0004* (2022.02); *A61B 1/00066* (2013.01); *A61B 1/018* (2013.01); *A61B 1/045* (2013.01); *A61B 1/051* (2013.01); *A61B 1/0655* (2022.02); *A61B 1/0676* (2013.01); *A61B 1/0684* (2013.01); *A61B 1/233* (2013.01); *A61B 1/00045* (2013.01)

(58) Field of Classification Search
CPC .............. A61B 1/00096; A61B 1/0004; A61B 1/00066; A61B 1/018; A61B 1/045; A61B 1/051; A61B 1/0655; A61B 1/0676; A61B 1/0684; A61B 1/233; A61B 1/00045
See application file for complete search history.

(56) References Cited

U.S. PATENT DOCUMENTS

| | | | | |
|---|---|---|---|---|
| 5,007,406 | A * | 4/1991 | Takahashi | B25J 1/02 600/119 |
| 2007/0249907 | A1* | 10/2007 | Boulais | A61B 5/064 600/179 |
| 2013/0116506 | A1* | 5/2013 | Bayer | A61B 1/00174 600/113 |
| 2015/0174363 | A1* | 6/2015 | Sutermeister | A61M 25/005 604/95.04 |
| 2018/0146839 | A1* | 5/2018 | Friedlander | A61B 1/00048 |
| 2018/0289242 | A1* | 10/2018 | Dai | A61B 1/0055 |

(Continued)

*Primary Examiner* — Timothy J Neal
(74) *Attorney, Agent, or Firm* — Farber LLC

(57) ABSTRACT

Systems and methods are disclosed for an endoscope for use in a surgical procedure, e.g., a pediatric trans-nasal endoscopy procedure. The endoscope may include a handle for gripping by a user, and a shaft extending from the handle. The shaft may have a working channel extending longitudinally therethrough and a distal region configured to be inserted into a patient. The distal region of the shaft may include a printed circuit board with a perpendicular portion having an illumination source mounted thereon so as to face distally. The printed circuit board may also have an imaging device mounted thereon, and the imaging device and the illumination source may be located at the same longitudinal position of the endoscope shaft, e.g., flush-mounted. The endoscope may also include, on the handle, an electronic control module having first and second buttons that are mapped to a menu of functions, e.g., white balancing and/or image capture functions, in an external video control unit.

15 Claims, 8 Drawing Sheets

(56) References Cited

U.S. PATENT DOCUMENTS

| | | | | |
|---|---|---|---|---|
| 2019/0357751 | A1* | 11/2019 | Friedlander | A61B 1/015 |
| 2020/0138271 | A1* | 5/2020 | Toth | A61B 1/0684 |
| 2020/0196434 | A1* | 6/2020 | Kuo | H04N 23/57 |
| 2021/0137349 | A1* | 5/2021 | Toth | A61B 1/00055 |
| 2021/0235978 | A1* | 8/2021 | Yan | A61B 1/00124 |
| 2021/0364778 | A1* | 11/2021 | Loo | G02B 23/243 |
| 2022/0022740 | A1* | 1/2022 | Truckai | A61B 1/00119 |
| 2022/0061645 | A1* | 3/2022 | Jochumsen | A61B 1/0011 |
| 2022/0095887 | A1* | 3/2022 | Lent | A61B 1/00117 |
| 2022/0107491 | A1* | 4/2022 | Brooks | A61B 1/0676 |
| 2022/0175226 | A1* | 6/2022 | Sørensen | A61B 1/00043 |
| 2022/0304559 | A1* | 9/2022 | Weeks | A61B 1/0655 |
| 2022/0395160 | A1* | 12/2022 | Salman | A61B 1/0669 |

\* cited by examiner

ENDOSCOPY DEVICE HAVING AN ELECTRICAL CONTROL SYSTEM

BACKGROUND

Eosinophilic esophagitis (EoE) is an increasingly common chronic inflammatory disease that affects children and adults. Because of its potential to progress to esophageal stricture and the fact that symptoms do not always correlate with degree of eosinophilia, much attention has been paid to repeated assessment of the esophageal mucosa to ensure mucosal healing following treatment. In contrast, the risks, cost and time commitment associated with traditional sedated esophagogastroduodenoscopy (EGD) can be significant and have raised concerns for providers and patients alike. To address these questions, alternative methods are needed to measure esophageal inflammation. In addition to esophagoscopy with biopsies, other technologies such as the Cytosponge, esophageal string test and confocal tethered endomicroscopy have emerged as potential alternatives for assessing mucosal inflammation.

Recent work has led to the development of trans-nasal endoscopy/esophagoscopy (TNE) to assess the esophageal mucosa in adults. In contrast to traditional EGDs, TNE offers advantages, including that it can be performed in an outpatient clinic room, requires no anesthesia or sedation, uses an adult trans-nasal gastroscope that is tolerated by adults and procures samples adequate for assessment of Barrett's Esophagus. However, the endoscopes used in the adult procedures are not appropriate for use in pediatric setting and, in fact, may be too large for many adults.

During a trans-nasal endoscopic procedure, patients may experience physical discomfort due to the endoscope being inserted into the nose, through the sinus cavities and down into the esophagus. This physical discomfort, or even the fear of being uncomfortable, can make trans-nasal endoscopy procedures mentally and emotionally distressing for a patient, too. Because it is desirable to make the procedure mentally and physically easier on the patient, it would be advantageous to optimize the endoscope being used for the procedure.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

In various embodiments, the trans-nasal endoscope addresses many challenges experienced by other systems. For example, the trans-nasal endoscope, according to various embodiments, provides a device and associated methodology that can be used to adapt TNE to assess the esophageal mucosa, gastric, and duodenal, tracheal, and bronchial mucosa in children and small adults in both a sedated and unsedated manner with a full array of steering and visualization capabilities. The trans-nasal endoscope, according to various embodiments, provides a scope that minimizes the outer diameter thereof, e.g., to reduce the discomfort to patients, while maximizing the diameter of the working channel, e.g., to provide the largest possible channel through which tools may be introduced, while simultaneously providing enhanced, e.g., four-way, steering capabilities as well as visualization functionality, as will be described more fully below. In various embodiments, the outer diameter of the endoscope shaft may be less than about 4.5 mm, and preferably is about 3.5 mm. In addition, in various embodiments, the diameter of the working channel may have a range of about 1.5 mm to 2.5 mm, and preferably is about 2.0 mm.

It is noted that, according to various embodiments, the endoscope described herein may be particularly well-suited for unsedated surgical procedures. Sedation is well-known, in certain circumstances, to present various risks to patients, but is often employed during surgical procedures to prevent a patient from experiencing discomfort or anxiety. By providing an endoscope having, e.g., a minimized outer diameter, a more flexible and more steerable distal regions (as will be explained in further detail below) among other advantages described below, patient discomfort and anxiety may be reduced, thereby enabling surgical procedures to be performed in an unsedated, and thus more safe, manner.

It should be recognized that, while the scope set forth herein is described for use in a trans-nasal endoscopy procedure, it may also be employed in a variety of other medical or surgical applications. For example, the scope set forth herein may be employed for use as a nasal endoscope, a trans-nasal esophagoscope, a trans-nasal gastroscope, a trans-nasal duodenoscope, a trans-nasal enteroscope, a triple endoscope, a bronchoscope, a laryngoscope, a trans-nasal gastroscope, an aerodigestive scope, and/or an endoscopic device used to visualize any body cavity into which it would fit, e.g., for examination of a stricture or the like. It should also be recognized that the endoscope described herein may be employed in fetal surgical procedures, and/or in surgical procedures that employ natural orifices, e.g., NOTES or natural orifice transluminal endoscopic procedures, such as trans-orally, trans-anally, trans-vaginally or any other natural orifice. The discussion herein of a pediatric trans-nasal endoscopy procedure is merely exemplary.

In accordance with various embodiments thereof, systems and methods are provided for use in a surgical procedure, e.g., a trans-nasal endoscopy procedure. In an embodiment, there is provided an endoscope for use in a surgical procedure. The endoscope may include a handle for gripping by a user, and a shaft extending from the handle. The shaft may have a working channel extending longitudinally therethrough, and a distal region configured to be inserted into a patient. The endoscope may also include a circuit board, e.g., a printed circuit board, located at the distal region of the shaft, the printed circuit board having a distal portion that is angled, e.g., perpendicular, relative to a proximal portion of the printed circuit board. The endoscope may also include an illumination source mounted on the distal portion of the printed circuit board such that the illumination source faces distally.

The endoscope may also include a camera sensor mounted on the printed circuit board. A distalmost face of the imaging device and a distalmost face of the illumination source may be located at the same longitudinal position of the endoscope shaft so as to be flush-mounted relative to a distalmost face of the shaft. In embodiments, the distalmost face of the shaft may be formed by a micro-molded tip component having an opening therein for the camera sensor and at least one pocket for receiving the illumination source. The distal portion of the printed circuit board may include two legs that are angled radially inwardly, and the illumination source may include an LED mounted on each leg. The two LEDs and the camera sensor may be positioned radially within the outer diameter of the shaft and radially outside the working channel so as not to impede the working channel.

The endoscope may also include an electrical cable extending longitudinally through the shaft from the printed circuit board to the handle. The electrical cable may be embedded between the outer diameter of the shaft and the inner diameter of the working channel so as to extend parallel to the working channel. The endoscope may also include an electronic control module on the handle, the electronic control module connected to the electrical cable within the handle. The electronic control module may include at least one of a white balancing button and an image capture button.

The endoscope may also include a video output cable extending from the handle, and a video control unit connectable to the video output cable. The video control unit may be configured to receive a signal from the at least one of a white balancing button and an image capture button. The endoscope may also include a video display device connectable to the video control unit. The video control unit may be configured, upon receiving the signal from the at least one of the white balancing button and the image capture button, to control at least one corresponding aspect of a video display on the video display device.

In still further embodiments, there may be provided an endoscope for use in a surgical procedure, e.g., a trans-nasal endoscopy procedure. The endoscope may include a handle for gripping by a user. The endoscope may also include a shaft extending from the handle. The shaft may have a working channel extending longitudinally therethrough, and a distal region configured to be inserted into a patient. The endoscope may also include a circuit board, e.g., printed circuit board, located at the distal region of the shaft, the printed circuit board including a first distal portion having an imaging device mounted thereon. The printed circuit board may also include a second distal portion that is angled, e.g., perpendicularly, relative to the printed circuit board, which may have an illumination source mounted thereon. A distalmost face of the imaging device and a distalmost face of the illumination source may be located at the same longitudinal position of the endoscope shaft.

In an embodiment, the illumination source may face distally. In addition, the second distal portion of the printed circuit board may include two legs that are bent radially inwardly, and the illumination source may include an LED mounted on each leg. The two LEDs and the imaging device may be positioned radially within the outer diameter of the shaft and radially outside the working channel so as not to impede the working channel.

In embodiments, the endoscope may also include an electrical cable extending longitudinally through the shaft from the printed circuit board to the handle. The electrical cable may be radially disposed between the outer diameter of the shaft and the inner diameter of the working channel so as to extend parallel to the working channel. The endoscope may also include an electronic control module on the handle, the electronic control module connected to the electrical cable within the handle. The electronic control module may include at least one of a white balancing button and an image capture button.

In still further embodiments, the endoscope may also include a video output cable extending from the handle, and a video control unit connectable to the video output cable. The video control unit may be configured to receive a signal from the at least one of the white balancing button and the image capture button. The endoscope may also include a video display device connectable to the video control unit. The video control unit may be configured, upon receiving the signal from the at least one of the white balancing button and the image capture button, to control at least one corresponding aspect of a video display on the video display device.

In still further embodiments, there is provided an endoscope for use in a surgical procedure, e.g., a trans-nasal endoscopy procedure. The endoscope may include a handle for gripping by a user, and a shaft extending from the handle. The shaft may have a working channel extending longitudinally therethrough, and a distal region configured to be inserted into a patient. The endoscope may also include an illumination source and a camera sensor mounted at the distal region of the shaft. The camera sensor may be configured for generating image signals related to the surgical procedure. The endoscope may also include an electronic control module on the handle, the electronic control module including a first button configured to transmit a first signal upon being pressed, and a second button configured to transmit a second signal upon being pressed. The endoscope may also include an external video control unit, the external video control unit including a menu of different video control functions. The external video control unit may be pre-programmed such that the first signal is mapped to a first function from the menu of video control functions so that the external video control unit causes the first function to be performed when the first button is pressed. The external video control unit may also be pre-programmed such that the second signal is mapped to a second function from the menu of video control functions so that the external video control unit causes the second function to be performed when the second button is pressed.

In further embodiments, the endoscope may also include a video display device connected to the external video control unit and configured to provide a display corresponding to the image signals generated by the camera sensor. The external video control unit may cause the first or second functions to be performed by the video display device, such that the video display device changes at least one aspect of the display based on the first or second function.

In still further embodiments, the endoscope may also include a video output cable extending from the handle to the external video control unit. The video output cable may be configured to transmit the image signals generated by the camera sensor, and to transmit the first and second signals from the first and second buttons to the external video control unit. The first button may be a white balancing button, wherein the external video control unit is pre-programmed such that the first signal is mapped to a white balancing function from the menu of video control functions, so that the external video control unit causes a white balancing function to be performed when the white balancing button is pressed. The second button may be an image capture button, wherein the external video control unit is pre-programmed such that the second signal is mapped to an image capture function from the menu of video control functions, so that the external video control unit causes the image capture function to be performed when the image capture button is pressed. The menu of video control functions may include, in addition to a white balancing function and an image capture function, other functions such as a zoom function, a video capture start function, a video capture stop function, a brightness change function, a start video conference function, a change color spectrum function, a zoom picture function, a magnify picture function, a measure size of object function, a measure distance of object function, and a launch program or any other keyboard function on an external computer.

In additional embodiments, the endoscope may also include a circuit board located at the distal region of the shaft. The circuit board may have the illumination source and the camera sensor mounted thereon. The endoscope may also include an electrical cable extending longitudinally through the shaft from the circuit board to the handle.

It should be noted, of course, that to the extent that images, e.g., image signals, image data, etc., are described herein, it will be understood that such also refers to video, e.g., video signals, video data, etc., and that the description of the image signals is intended to include single images, still images, video images, etc. without limitation.

DRAWINGS

Figure 8:
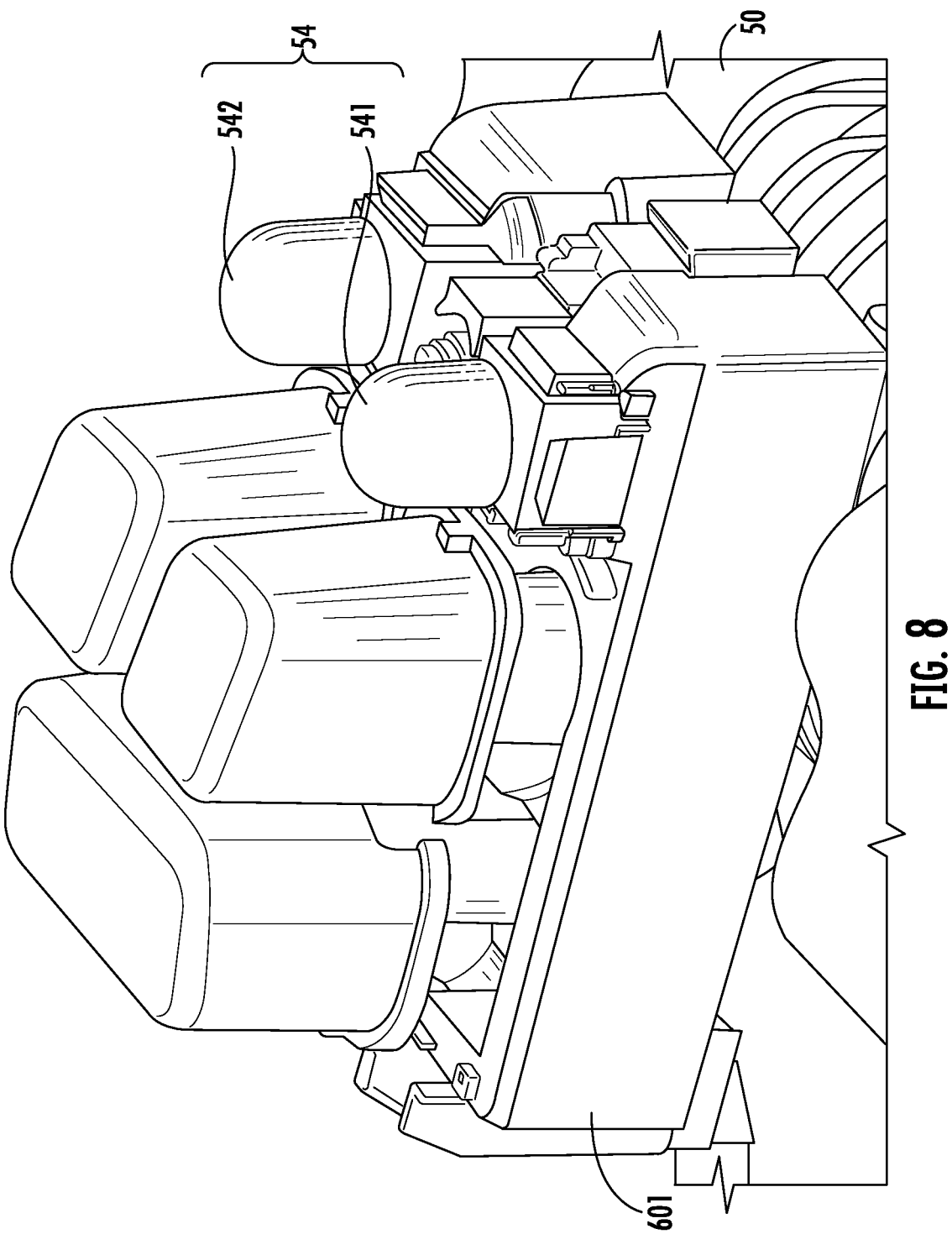

FIG. 8. is a perspective view (with various components being hidden so as not to obscure the features shown) of an electronics control module, in accordance with various embodiments.

DETAILED DESCRIPTION

Reference will now be made in detail to specific embodiments illustrated in the accompanying drawings. In the following detailed description, numerous specific details are set forth to provide a thorough understanding. However, it will be apparent to one of ordinary skill in the art that embodiments may be practiced without these specific details. In other instances, known methods, procedures, components, circuits, and networks have not been described in detail so as not to unnecessarily obscure aspects of the embodiments.

Figure 1:
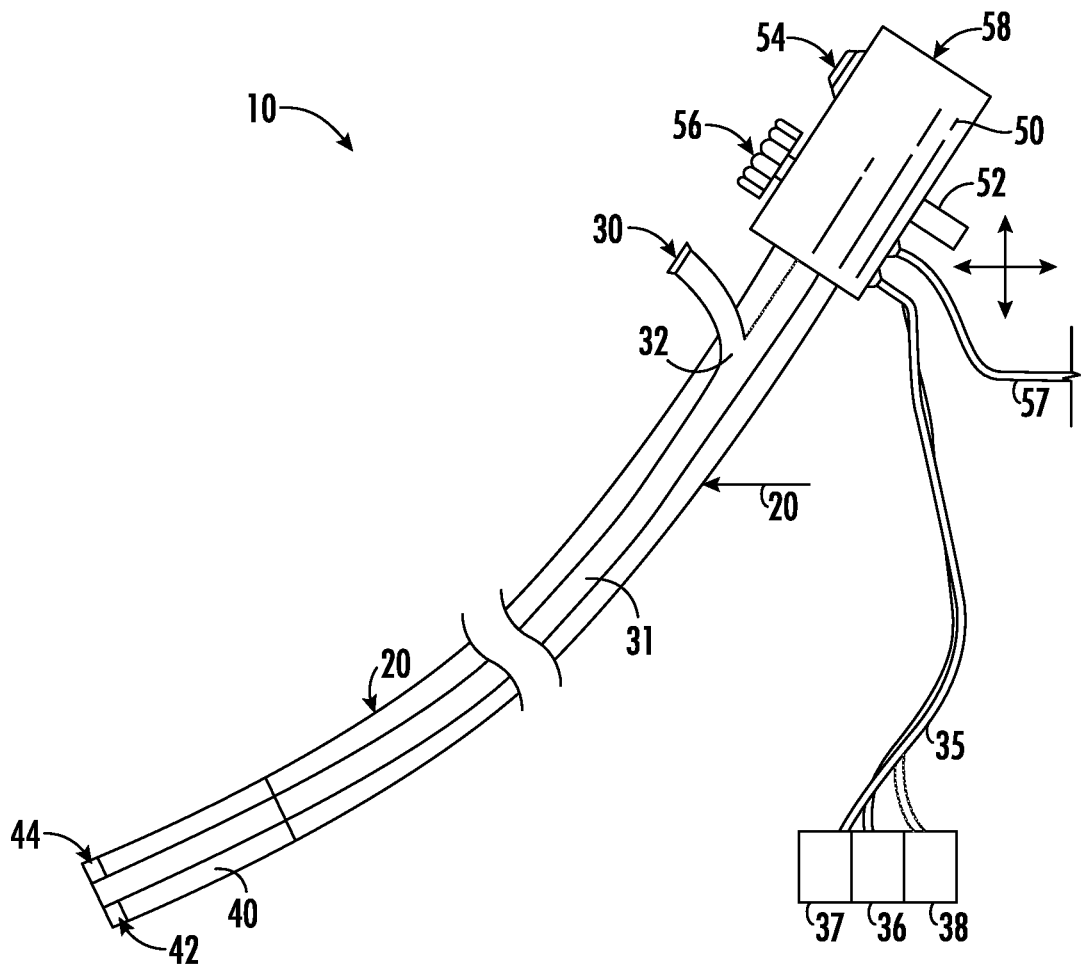
FIG. 1 shows a schematic representation of a trans-nasal endoscope that includes a flexible endoscope shaft, in accordance with various embodiments.

FIG. 1 is a schematic diagram of a trans-nasal endoscope 10, according to one example embodiment, illustrating some of the various features thereof. As mentioned previously, while the example embodiments set forth hereinbelow are described as an endoscope that is suitable for trans-nasal insertion into a patient, and is particularly well-suited for trans-nasal insertion into a child or small adult, it is understood that this is merely one example embodiment, and that the description hereinbelow of a trans-nasal endoscope does not preclude the use of the device in other types of procedures and for other types of patients. It should be noted that FIG. 1 is merely schematic, and thus the shape and position of the various features illustrated therein are merely exemplary. Additional figures, illustrating specific embodiments of the various features and functionality, will be provided in further detail below.

In the embodiment shown schematically in FIG. 1, the trans-nasal endoscope 10 includes a flexible endoscope shaft 20. The flexible endoscope shaft 20 has a working channel 31. The working channel 31 extends longitudinally from a distal end 40 of the endoscope shaft 20 proximally towards a handle 50 located at or near the proximal end of the trans-nasal endoscope 10. At, within or near the handle 50, the working channel 31 has a bifurcation region 32. Proximal to the bifurcation region 32, the working channel 31 splits into two channels. A first portion of the working channel 31 proximal to the bifurcation regions 32 extends towards an instrument insertion port 30 suitable for, e.g., conducting a biopsy therethrough. The instrument insertion port 30 allows an instrument, e.g., a pediatric nasal endoscope biopsy forceps or other medical device, to be inserted through the bifurcation region 32 and to, and past, the distal end 40 of the endoscope shaft 20 so as to perform a procedure, e.g., a biopsy procedure, on tissue located at or near to the distal end 40 of the endoscope shaft 20.

A second portion of the working channel 31 proximal to the bifurcation regions 32 extends towards an air, water and suction (AWS) control mechanism 52. The AWS control mechanism 52 includes various valves (not shown in this view, but shown and described in greater detail in Applicant's co-pending U.S. patent application Ser. No. 18/108, 558, filed on the same date as this present application, which is hereby incorporated by reference herein in its entirety) that allow selective connection of the working channel 31 to the AWS tubing set 35. The AWS tubing set 35 may include one or more flexible tubes (shown and described separately and in greater detail in Applicant's co-pending U.S. patent application Ser. No. 18/108,558). The AWS tubing set 35 may be connected to a water source 37 for supplying water through the working channel 31, to a suction source 36 for supplying suction through the working channel 31, and/or to an air source 38 for supplying air through the working channel 31, depending upon a user's selection via the AWS control mechanism 52. More specifically, the AWS control mechanism allows a user to direct one or more of air, suction or water through, e.g., the bifurcation region 32 and to, and past, the distal end 40 of the endoscope shaft 20 so as to enable their use during the performance of a procedure on tissue located at or near the distal end 40 of the endoscope shaft 20.

The distal end 40 of the endoscope shaft 20 also includes an illumination source 42 to provide light at the distal end 40. In embodiments, the illumination source 42 may be connected to and at least partially controllable by an electronics control module 54 located in the handle 50. The distal end 40 of the endoscope shaft 20 also includes an image capture device 44 to convey image or video signals related to the region of the distal end 40 of the endoscope shaft 20. In embodiments, the image capture device 44 may also be connected to and at least partially controllable by the electronics control module 54 located in the handle 50. The handle 50 may also include a shaft steering mechanism 56 to control or steer the lateral displacement at the distal end 40 of the endoscope shaft 20. In addition, the handle 50 may include a video display output 57, which may be connected to and output image data to a separate image or video display or control unit (not shown in this view).

Figure 2:
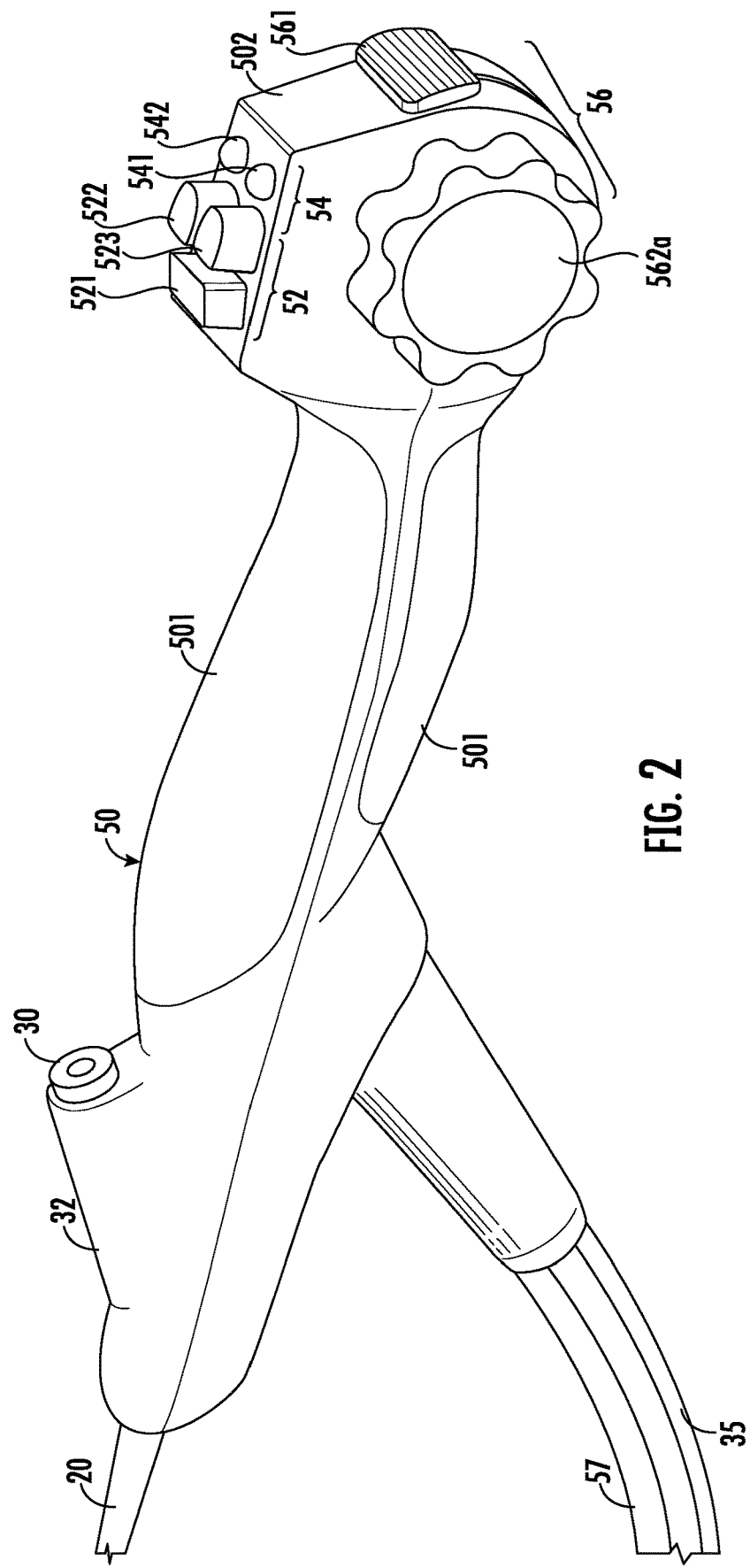
FIG. 2 is a perspective view of the handle of the trans-nasal endoscope, in accordance with various embodiments.

FIG. 2 is a perspective view of an example embodiment of the handle 50 of the trans-nasal endoscope 10. In this embodiment, the features and functionality that were shown schematically in FIG. 1 are provided in more detail, showing additional advantages thereof. For example, in this embodiment, the handle 50 of the trans-nasal endoscope 10 includes a gripping region 501 sized and contoured to fit comfortably in a user's hand. Located distally relative to the gripping region 501 is the bifurcation region 32. From the distalmost end of the bifurcation region 32 extends the flexible endoscope shaft 20, having a portion of the working channel 31 (not shown in this view) extending therethrough. The working channel 31 extends from the distal end 40 of the endoscope shaft 20, and splits into two channels in the bifurcation region 32. A first portion of the working channel 31 extends towards the instrument insertion port 30, which is suitable for receiving an instrument, e.g., a pediatric nasal endoscope biopsy forceps or other medical device, therethrough. The second portion of the working channel 31 proximal to the bifurcation region 32 extends proximally through the interior of the gripping region 501.

Proximal to the gripping region 501 is a control region 502 sized and shaped to extend beyond the heel of the user's hand when the palm of the user's hand is gripping the gripping region 501, enabling the control features positioned on the control region 502 to be engaged by the user's second hand when the user's first hand is gripping the gripping region 501.

In the embodiment shown in FIG. 2, the control region 502 has various control features positioned thereon. For example, the control region 502 has the AWS control mechanism 52. As set forth above, the AWS control mechanism 52 includes various features, e.g., buttons, valves, etc., that allow selective connection of the air, water and suction supply sources 36, 37, 38 to the working channel 31 via respective flexible tubes of the AWS tubing set 35. In the embodiment shown in FIG. 2, the AWS control mechanism 52 includes an air supply control button 521. The air supply control button 521 functions to selectively connect the air source 38 to the working channel 31, as is described in greater detail in Applicant's co-pending U.S. patent application Ser. No. 18/108,558.

In the embodiment shown in FIG. 2, the AWS control mechanism 52 also includes a water supply control button 522. The water supply control button 522 functions to selectively connect the water source 37 to the working channel 31, as is described in greater detail in Applicant's co-pending U.S. patent application Ser. No. 18/108,558.

Still further, in the embodiment shown in FIG. 2, the AWS control mechanism 52 includes a suction supply control button 523. The suction supply control button 523 functions to selectively connect the suction source 36 to the working channel 31, as is described in greater detail in Applicant's co-pending U.S. patent application Ser. No. 18/108,558.

In the embodiment shown in FIG. 2, the control region 502 also has the electronics control mechanism 54. As set forth above, the electronics control mechanism 54 includes various features, e.g., buttons, electrical connections, etc., that allow selective operations related to, e.g, the image capture device 44 and/or the illumination device 44 located at the distal end 40 of the endoscope shaft 20. In the embodiment shown in FIG. 2, the electronics control mechanism 54 includes a first, e.g., a white balance control, button 541. In this embodiment, the white balance control button 541 functions to selectively control a white balancing operation by sending a corresponding signal to an image or video control unit (not shown), as is described in greater detail below in FIGS. 7 and 8.

In the embodiment shown in FIG. 2, the electronics control mechanism 54 also includes a second, e.g., an image capture control, button 542. In this embodiment, the image capture control button 542 functions to selectively control the capture of image or video signals sent by the image capture device 44, e.g., such as by providing a signal to an image or video display or control unit (not shown), as is described in greater detail below in connection with FIGS. 7 and 8.

In the embodiment shown in FIG. 2, the control region 502 also has the shaft steering mechanism 56. As set forth above, the shaft steering mechanism 56 includes various features, e.g., knobs, rollers, etc., that allow a user to control or steer the lateral displacement at the distal end 40 of the endoscope shaft 20. In the embodiment shown in FIG. 2, the shaft steering mechanism 56 includes a first knob 561 for controlling a first movement of the distal end 40 of the endoscope shaft 20, as is described in greater detail in Applicant's co-pending U.S. patent application Ser. No. 18/108,562, filed on the same date as this present application, which is hereby incorporated by reference herein in its entirety. FIG. 2 also illustrates the shaft steering mechanism 56 including opposing roller knobs 562a, 562b (knob 562b being hidden from view in FIG. 2, but being located on the opposite side of the handle 50) for controlling additional movements of the distal end 40 of the endoscope shaft 20. Additional features and functionality of the shaft steering mechanisms 56, such as steering wires 302a, 302b, 302c, 302d, are shown and described in greater detail in Applicant's co-pending U.S. patent application Ser. No. 18/108, 562.

In addition, in the embodiment shown in FIG. 2, the handle 50 of the trans-nasal endoscope 10 includes a connection to the AWS tubing set 35. As set forth above, the AWS tubing set includes various flexible tubes that connect to the suction source 36, the water source 37 and the air source 38, as is described in greater detail in Applicant's co-pending U.S. patent application Ser. No. 18/108,558. Still further, the handle 50 includes a connection to a video display output 57, e.g., for connecting to and outputting image data and/or signals to a separate video display or control unit (not shown in FIG. 2). In the embodiment shown in FIG. 2, the video display output 57 is bundled together with the AWS tubing set 35.

Figure 3:
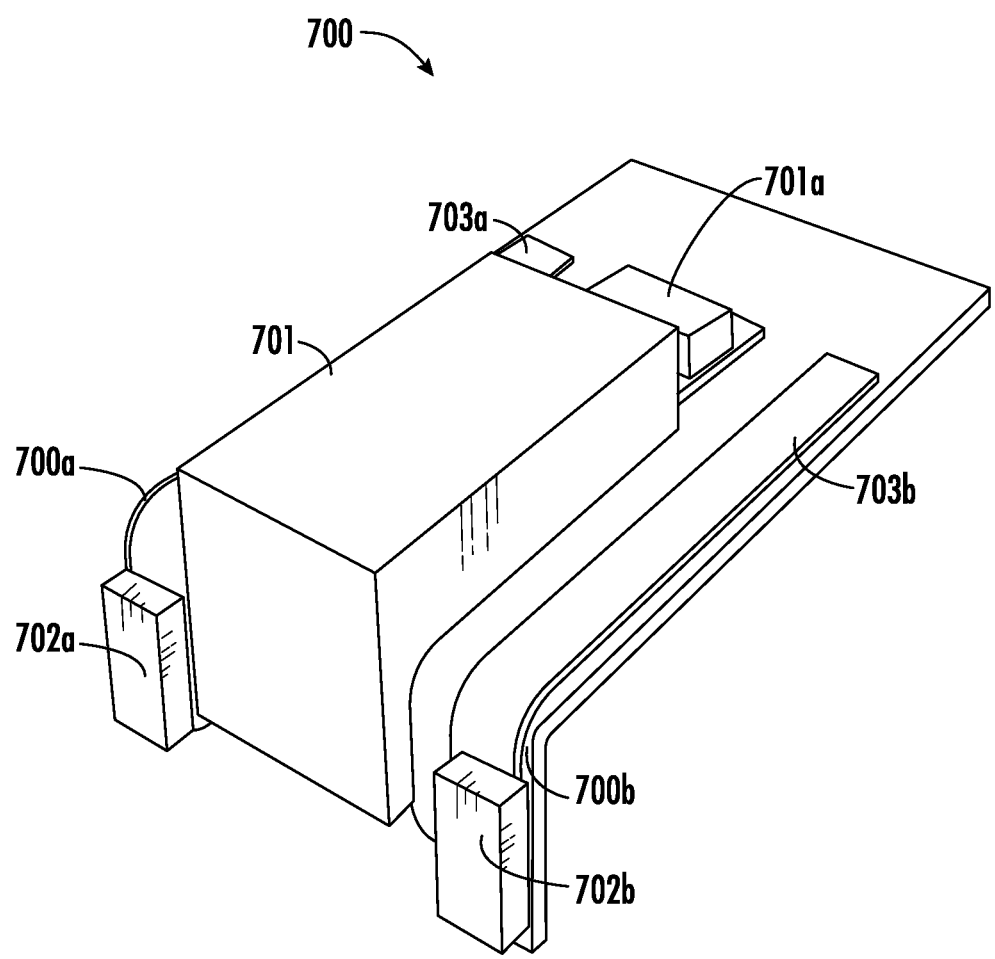
FIG. 3 illustrates a front perspective view of a printed circuit board (PCB) that may be employed in the endoscope shaft, in accordance with various embodiments.

As set forth above on connection with FIG. 1, the distal end 40 of the endoscope shaft 20 may include an illumination source 42, e.g., to provide light at the distal tip 40, and an image capture device 44, e.g., to convey image or video signals related to the region of the distal end 40 of the endoscope shaft 20. FIG. 3 illustrates a front perspective view of a printed circuit board (PCB) 700 that may be employed in the endoscope shaft 20, according an embodiment. More specifically, FIG. 3 illustrates a front perspective view of a circuit board, e.g., a printed circuit board 700, that may be employed at the distal-most end 40 of the endoscope shaft 20 to provide light and generate image signals during a surgical procedure, according an embodiment.

In the embodiment shown, the printed circuit board 700 includes the imaging device 44, in the form of, e.g., a camera sensor 701. It is noted that the imaging device 44 may be any device configured to detect light reflected from the light source 42 and output an image signal. The imaging device 44 can be, for example, a charged coupled device ("CCD") or other suitable imaging sensor. In some embodiments, the imaging device 44 may include at least two lenses providing stereo imaging, or can be an omnidirectional camera.

In the embodiment shown, the camera sensor 701 is located in the center of the printed circuit board 700. FIG. 3 also shows that the printed circuit board 700 includes a connection site 701*a* at which the camera sensor 701 may be connected to a data cable, such as a camera electrical cable 301 that extends longitudinally along the endoscope shaft 20, as will be shown and described in greater detail below in connection with FIG. 4.

In the embodiment shown, the printed circuit board 700 also includes the illumination source 42, e.g., in this case in the form of a pair of LEDs 702*a* and 702*b*. Of course, in other embodiments, a single illumination source, e.g., a single LED may be employed. Furthermore, it should be recognized that, in other embodiments, illumination sources other than LEDs, e.g., a halogen bulb, an incandescent bulb, or other suitable light emitter may be employed. Returning to the embodiment shown in FIG. 3, the pair of LEDs 702*a*, 702*b* may be located in opposite sides of the camera sensor 701, so as to be positioned at or near to the opposite lateral edges of the printed circuit board 700. FIG. 3 also shows that the printed circuit board 700 includes connection sites 703*a*, 703*b* at which the pair of LEDs 702*a*, 702*b* may respectively be connected to a data cable, such as a camera electrical cable 301 that extends longitudinally along the endoscope shaft 20, as will be shown and described in greater detail below in connection with FIG. 4.

Advantageously, the pair of LEDs 702*a*, 702*b* may be configured so as to face distally. In this way, the pair of LEDs 702*a*, 702*b* may provide increased illumination in a forward-facing direction, thereby primarily illuminating that region within a patient that is located directly in front of the distal end 40 of the endoscope shaft 20. In the embodiment shown, the pair of LEDs 702*a*, 702*b* is configured so as to face distally by virtue of distal leg portions 700*a*, 700*b* of the printed circuit board 700, and the pair of LEDs 702*a*, 702*b* mounted thereon, being bent downwardly, e.g., radially inwardly (in this view) at, e.g., an approximately 90 degree angle so as to be perpendicular, or generally perpendicular, relative to the proximal portion of the printed circuit board 700.

Still further, the printed circuit board 700 may be configured, in accordance with certain embodiments, such that the distal-most face of the pair of LEDs 702*a*, 702*b* is flush, e.g., equidistant in a longitudinal direction, with a distal-most face of the camera sensor 701. Having the distal-most face of the pair of LEDs 702*a*, 702*b* be flush with a distal-most face of the camera sensor 701 may provide several advantages. For example, having the distal-most face of the pair of LEDs 702*a*, 702*b* be flush with a distal-most face of the camera sensor 701 improves the image quality provided by the image capture device 44, for example, because the light provided by the pair of LEDs 702*a*, 702*b* does not contribute to or cause excessive glare or backlight reflection, as may occur in configurations in which the pair of LEDs 702*a*, 702*b* are located either more distal than, or more proximal than, the distal-most face of the camera sensor 701.

Figure 4:
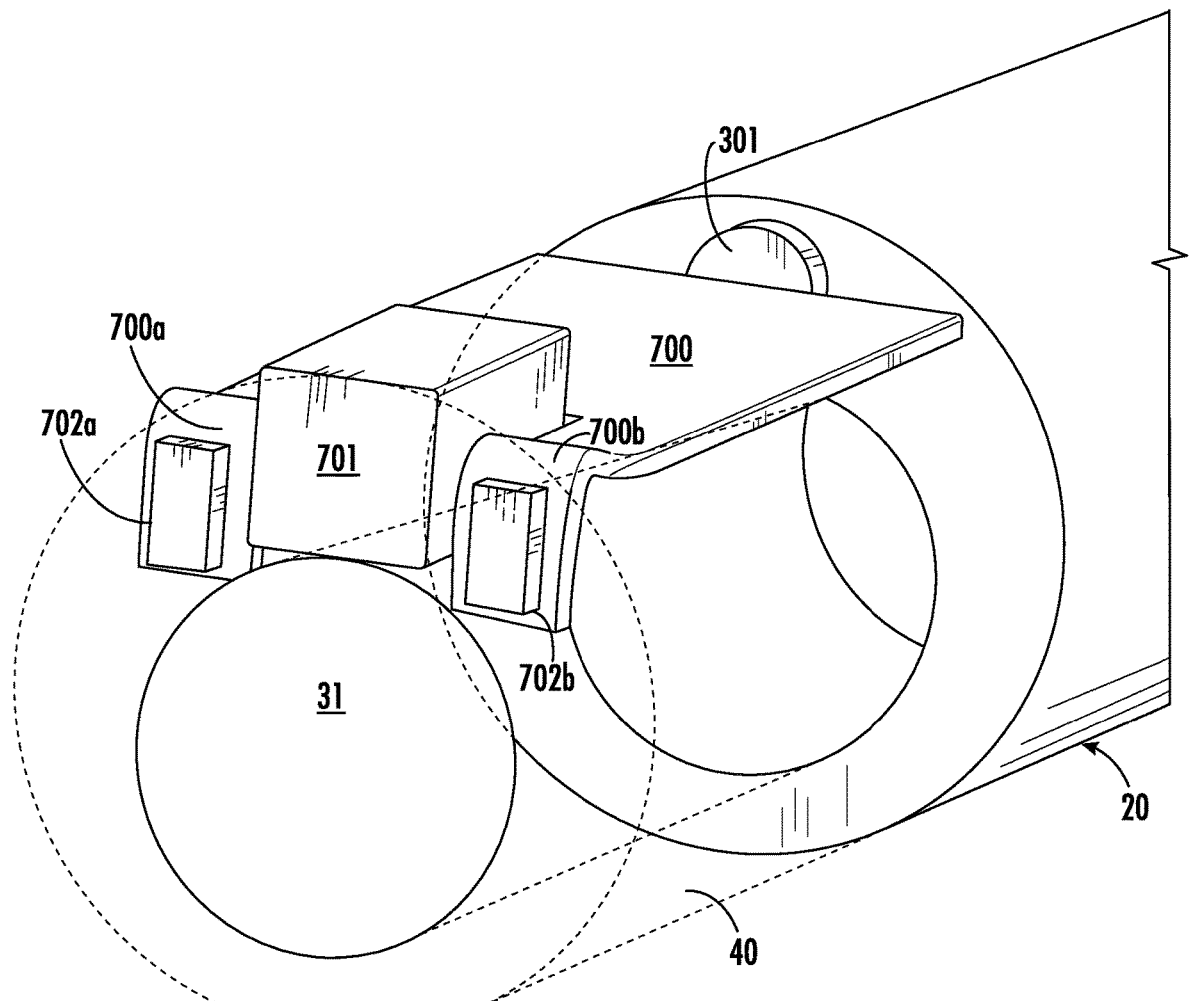
FIG. 4 is a front perspective view of the distal end of the endoscope shaft, in accordance with various embodiments.

FIG. 4 is a front perspective view of the distal end 40 of the endoscope shaft 20, according to an embodiment. In FIG. 4, some components of the endoscope shaft 20 are hidden or shown in phantom so as not to obscure the features shown. In the embodiment shown, the proximal end of the printed circuit board 700 may abut, or otherwise be adjacent to a camera electrical cable 301 extending longitudinally through the endoscope shaft 20. In this way, the pair of LEDs 702*a*, 702*b* are advantageously positioned so as to each be connected to the camera electrical cable 301, e.g., by soldering thereto. Likewise, by the proximal end of the printed circuit board 700 abutting or otherwise being adjacent to the camera electrical cable 301, the camera sensor 701 may also be advantageously positioned so as to also be connected to the camera electrical cable 301, e.g., by soldering thereto.

As set forth above, the printed circuit board 700 may be configured, in accordance with certain embodiments, such that the distal-most face of the pair of LEDs 702*a*, 702*b* is flush, e.g., equidistant in a longitudinal direction, with a distal-most face of the camera sensor 701. As shown in FIG. 4, in certain embodiments, the distal-most face of the pair of LEDs 702*a*, 702*b* and the distal-most face of the camera sensor 701 may not only be flush relative to each other, but may also be flush relative to the distal-most face of the endoscope shaft 20. In this embodiment, in addition to the advantages set forth above in connection with having the distal-most face of the pair of LEDs 702*a*, 702*b* be flush with the distal-most face of the camera sensor 701 (e.g., less glare and/or backlight reflection, etc), having the distal-most face of the pair of LEDs 702*a*, 702*b* and the distal-most face of the camera sensor 701 also be flush relative to the distal-most face of the endoscope shaft 20 may have still further advantages. For example, having the distal-most face of the pair of LEDs 702*a*, 702*b* and the distal-most face of the camera sensor 701 also be flush relative to the distal-most face of the endoscope shaft 20 may simplify manufacturing, in that a relative flat surface is provided at the distal-most face of the endoscope shaft 20 for any protective layer, e.g., coating or laminate etc., that may be applied to such distal-most face of the endoscope shaft 20. Furthermore, having the distal-most face of the pair of LEDs 702*a*, 702*b* and the distal-most face of the camera sensor 701 also be flush relative to the distal-most face of the endoscope shaft 20 may simplify operation, in that a relative flat surface being provided at the distal-most face of the endoscope shaft 20 may help reduce the possibility that an instrument that is passed through the working channel of the endoscope shaft 20 is snagged on or otherwise undesirably contacts either of the pair of LEDs 702*a*, 702*b* or the camera sensor 701. Still further, having the distal-most face of the pair of LEDs 702*a*, 702*b* and the distal-most face of the camera sensor 701 also be flush relative to the distal-most face of the endoscope shaft 20 may help improve safety, in that a relative flat surface being provided at the distal-most face of the endoscope shaft 20 may help reduce the possibility that the distal-most face of the endoscope shaft 20 irritates or otherwise injures the sensitive tissue within a patient as the endoscope shaft 20 is introduced and inserted through the patient's nasal cavity, sinus cavity, esophagus, etc.

In this embodiment, the printed circuit board 700 is mounted within the shaft wall of the endoscope shaft 20. In the view shown, the printed circuit board 700 is positioned entirely within the shaft wall, e.g., such that all portions of the printed circuit board 700 are positioned laterally outside of the inner diameter of the working channel 31, while all portions of the printed circuit board 700 are positioned laterally within the outer diameter of the endoscope shaft 20. Having all portions of the printed circuit board 700 be positioned laterally outside of the inner diameter of the working channel 31, while also being positioned laterally within the outer diameter of the endoscope shaft 20, may provide several advantages. For example, having all portions of the printed circuit board 700 be positioned laterally outside of the inner diameter of the working channel 31, while also being positioned laterally within the outer diameter of the endoscope shaft 20, enables the working channel 31 to be completely clear of any obstructions. Enabling the working channel 31 to be completely clear of any obstructions may simplify manufacturing, e.g., in that any material that forms the endoscope shaft 20 or any protective layer or coating thereof may avoid the working channel 31. Furthermore, enabling the working channel 31 to be completely clear of any obstructions may simplify operation, in that an obstruction-free working channel 31 may help reduce the possibility that an instrument that is passed through the working channel 31 of the endoscope shaft 20 is snagged on or otherwise interferes with the function of, e.g., damaging or blocking the view of, the pair of LEDs 702a, 702b or the camera sensor 701 while within the working channel 31. Still further, enabling the working channel 31 to be completely clear of any obstructions may help improve safety, in that an obstruction-free working channel 31 may help reduce the possibility that an instrument inserted through the working channel 31 is damaged or otherwise impeded in its movement, which could negatively impact the surgical procedure, e.g., it could cause a biopsy sample to be harmed or dropped, it could cause broken components to be left behind in the surgical site, etc.

The configuration of the printed circuit board 700, and of the camera sensor 701 and the pair of LEDs 702a, 702b mounted thereon, as shown in FIG. 4, may also provide the advantage that the shaft wall of the endoscope shaft 20 may have the smallest thickness possible. Having the smallest wall thickness possible for the endoscope shaft 20 may help enable the endoscope shaft 20 to maximize the inner diameter of the working channel, e.g., so as to enable the largest range of instruments to be passed therethrough, while minimizing the outer diameter of the endoscope shaft 20, e.g., so as to cause as little discomfort to the patient as possible when the endoscope shaft 20 is inserted into the patient. This, in turn, may help to optimize the endoscope shaft for procedures such as, e.g., pediatric trans-nasal endoscopy procedures, for which these characteristics of the endoscope shaft 20 are particularly important.

As mentioned above, in the embodiment shown in FIG. 4, the pair of LEDs 702a, 702b is configured so as to face distally by virtue of distal leg portions 700a, 700b of the printed circuit board 700, and the pair of LEDs 702a, 702b mounted thereon, being bent downwardly, e.g., radially inwardly (in this view) at a 90 degree angle so as to be perpendicular relative to the proximal portion of the printed circuit board 700. Because the working channel 31 is round and its outer diameter thereby has a curvature, the distal legs 700a, 700b of the printed circuit board 700 are, in the embodiment shown, advantageously bent into a position such that the bottom-most edge of the LEDs 702a, 702b are positioned lower than (in this view) the bottom-most edge of the camera sensor 701. This positions the pair of LEDs 702a, 702b closer to the center of the working channel 31 than the pair of LEDs 702a, 702b would otherwise be were the distal legs 700a, 700b of the printed circuit board 700 instead bent into a position at which the bottom-most edge of the LEDs 702a, 702b were even with the bottom-most edge of the camera sensor 701. Thus, having the distal legs 700a, 700b of the printed circuit board 700 bent into a position such that the bottom-most edge of the LEDs 702a, 702b are positioned lower than the bottom-most edge of the camera sensor 701 helps to enable the wall thickness of the endoscope shaft 20 to be minimized, since this configuration follows the curvature of the working channel 31 and the outer diameter of the endoscope shaft 20. Still further, having the distal legs 700a, 700b of the printed circuit board 700 bent into a position such that the bottom-most edge of the LEDs 702a, 702b are positioned lower than the bottom-most edge of the camera sensor 701 positions the LEDs 702a, 702b closer to any tissue that is positioned directly in front of the working channel 31, thereby ensuring that such tissue is optimally lit by the pair of LEDs 702a, 702b during a surgical procedure.

Figure 5:
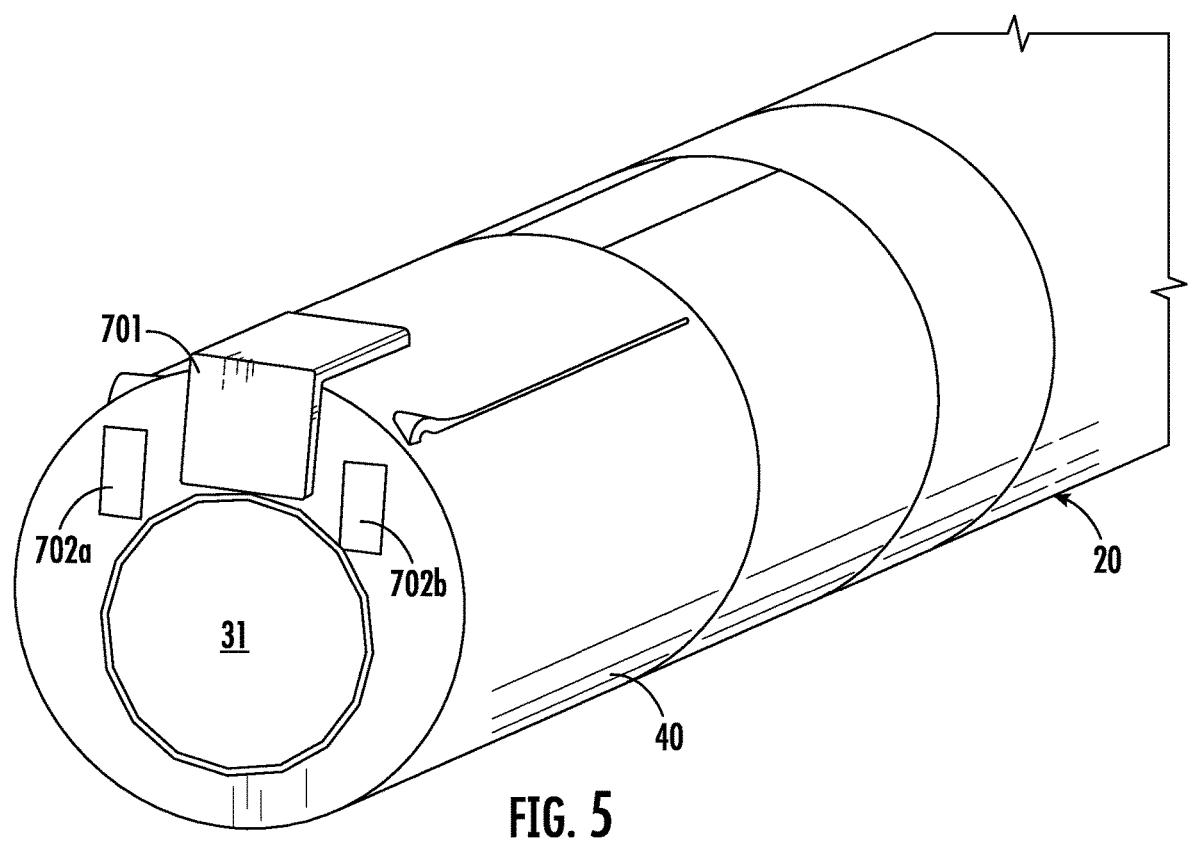
FIG. 5 is a front perspective view similar to that shown in FIG. 4, but having the distal region of the endoscope shaft enclosed by a protective layer, in accordance with various embodiments.
Figure 6:
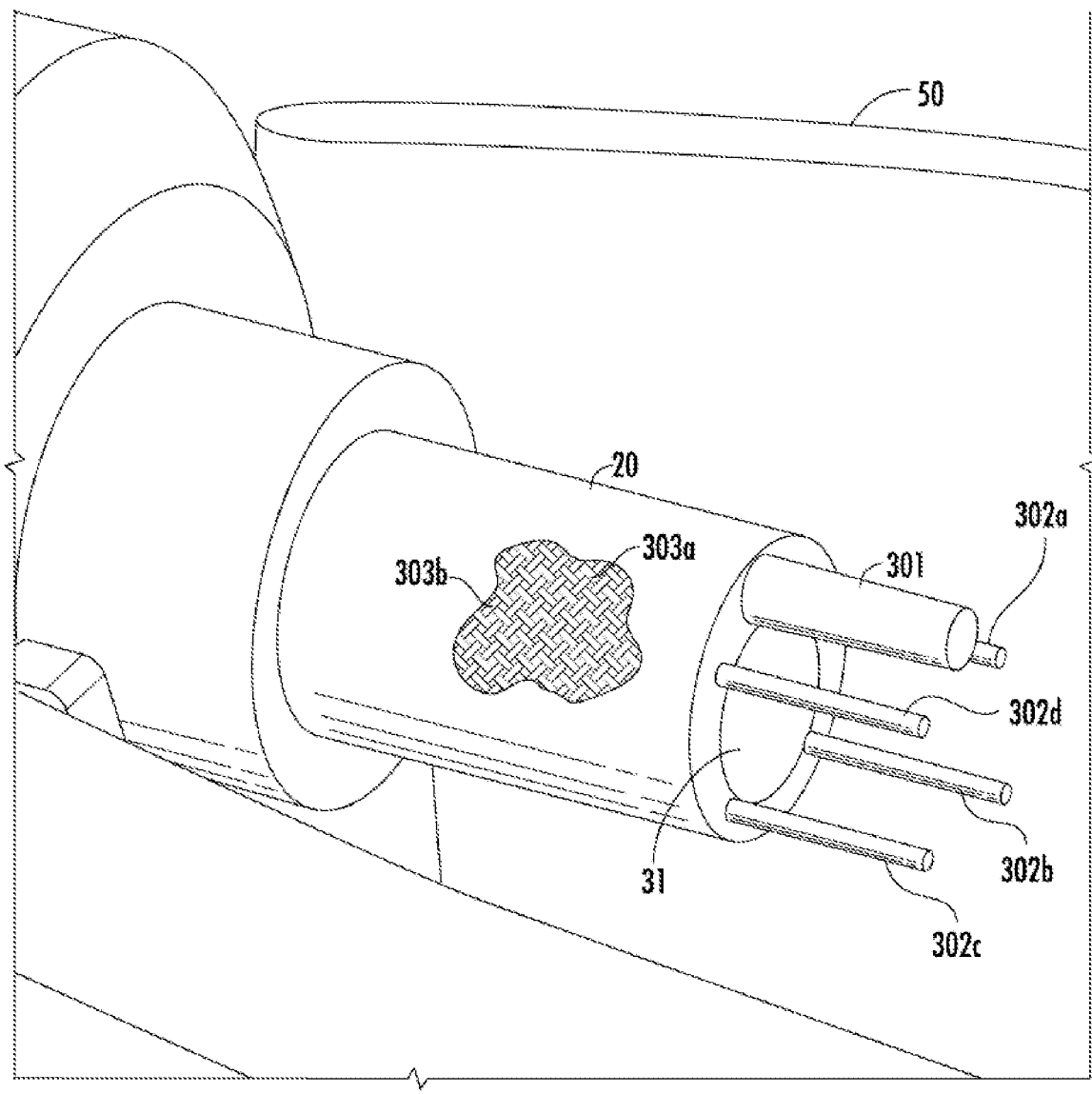
FIG. 6 is a perspective, cut-away view of the handle that illustrates a portion of a camera electrical cable as it extends into the handle, in accordance with various embodiments.

FIG. 5 is a front perspective view similar to that shown in FIG. 4, but having the distal region 40 of the endoscope shaft 20 enclosed by a protective layer. In various embodiments, the printed circuit board 700 may be mounted to the distal region 40 of the endoscope 20 via one or more of a pattern of braided filaments, e.g., braided filaments 303a, 303b (as shown in FIG. 6), the filaments being alternatingly woven over and under the printed circuit board 70 and around the working channel 31 so as to fix the printed circuit board 700 in position at the distal end of the endoscope 20. Additionally or alternatively, the printed circuit board 700 may be mounted to the distal region 40 of the endoscope 20, via a laminate layer of flexible polymer, such as Pebax® 35 (Pebax® being a tradename for a thermoplastic elastomer of polyether block amide, obtained by, e.g. polycondensation of a carboxylic acid polyamide with an alcohol termination polyether, available commercially from, e.g., Compounding Solutions in Lewiston, ME) or other suitable material. Various possible configurations for the endoscope shaft 20 being formed of a braided pattern of woven filaments and/or having protective laminate layers of flexible polymer are shown and described in additional detail in Applicant's co-pending patent application having client matter number EVO 1008-US. As shown in FIG. 5, neither the pair of LEDs 702a, 702b nor the camera sensor 701 impedes the distal opening into the working channel 31, thereby ensuring an obstruction-free passage of instruments therethrough.

In embodiments, the distalmost tip of the endoscope shaft 20 may be comprised of a micro-molded Pebax® 55D tip component that has an opening sized to accept the camera sensor 701. Such a micro-molded tip component may also include translucent pockets to the sides of the opening that situate the LEDs 702a, 702b adjacent to the camera sensor 701. Having the camera sensor 701 exposed through an opening in such a micro-molded tip component may, according to embodiments and as previously mentioned above, provide an arrangement in which material is not disposed in front of, e.g., distally relative to, the camera sensor 701, thereby preventing or reducing light filtration or distortion. In such an embodiment having pockets therein, the LEDs 702a, 702b may be maintained essentially flush with, or in some embodiments slightly proximal to, a face of the camera sensor 701 to prevent light from, e.g., bleeding, into the camera sensor 701. Still further, the distalmost edges of such a micro-molded tip may be contoured, or otherwise curved, such that the distalmost edges present an atraumatic surface to the patient during insertion and manipulation.

As shown and mentioned above in connection with FIG. 4, the proximal end of the printed circuit board 700 may abut, or otherwise be adjacent to, a distal end of a camera electrical cable 301 extending longitudinally through the endoscope shaft 20 such that the pair of LEDs 702a, 702b and the camera sensor 701 may each be connected to, e.g., by soldering, the distal end of the camera electrical cable 301. FIG. 6 is a perspective, cut-away view of the handle 50 that illustrates a different portion of the camera electrical cable 301, specifically a portion of the camera electrical cable 301 as it extends into the handle 50. FIG. 6 illustrates that, in accordance with embodiments, the camera electrical cable 301 extends longitudinally through the endoscope shaft 20 so as to be parallel to the working channel 31. As shown, the camera electrical cable 301 is embedded in, or otherwise disposed within, the wall of the endoscope shaft 20, such that is disposed laterally outside of the inner diameter of the working channel 31 but laterally inside of the outer diameter of the endoscope shaft 20. The camera electrical cable 301 emerges from the shaft wall of the endoscope shaft 20 into the handle 50, where it extends proximally to an electronics control module 54 located on a proximal portion of the handle 50 (shown in FIG. 8).

Figure 7:
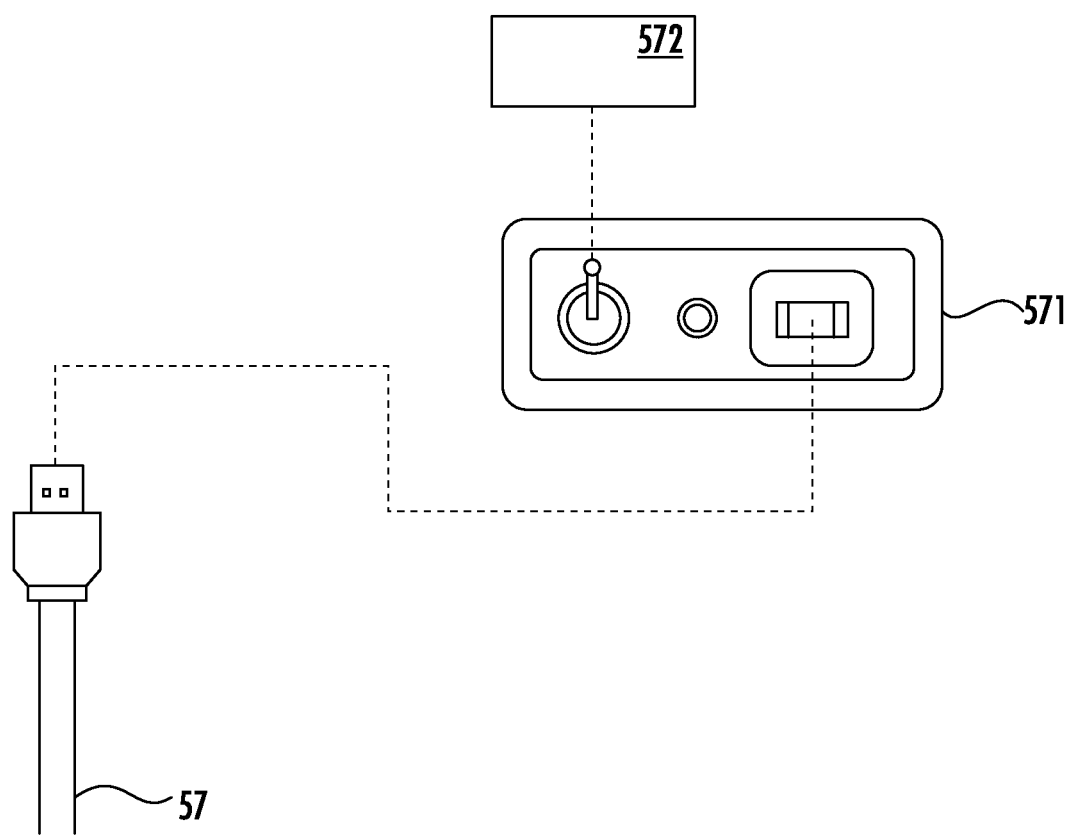
FIG. 7 is a schematic view of portions of a video display system, in accordance with various embodiments.

As mentioned above in connection with FIGS. 1 and 2, the trans-nasal endoscope 10 may include a video display output cable 57 that extends from the handle 50. FIG. 7 is a schematic view of portions of a video display system, according to various embodiments. As shown in FIG. 7, the proximal end of the video display output cable 57 is connectable to an external video control unit 571. The external video control unit 571 is, in turn, connectable to a video display device 572 configured to display images or video to a user.

In operation, when the proximal end of the video display output cable 57 is connected to the external video control unit 571, the external video control unit 571 sends power through the video display output cable 57 to the illumination source 42, e.g., the pair of LEDs 702a, 702b shown in FIGS. 3-5, so as to enable the illumination source 42 to provide light at the distal end 40 of the endoscope shaft 20. Likewise, when the proximal end of the video display output cable 57 is connected to the external video control unit 571, the external video control unit 571 sends power through the video display output cable 57 to the image capture device 44, e.g., the camera sensor 701 shown in FIGS. 3-5, so as to enable the image capture device 44 to generate image signals at the distal end 40 of the endoscope shaft 20. The image capture device 44 is then configured to send image signals, e.g., related to the tissue located in front of the distal end of the endoscope shaft 20 as lit up by the illumination source 42, back through the video display output cable 57 to the external video control unit 571.

These image signals, e.g., related to the tissue located in front of the distal end of the endoscope shaft 20, are received by the external video control unit 571 (via the video display output cable 57), which provides them to the video display device 572 for viewing by a user. In this way, according to various embodiments, a user can view on the video display device 572 a continuous video image of, e.g., the tissue located in front of the distal end of the endoscope shaft 20. This continuous video image may enable a user to more safely insert the distal end of the endoscope shaft 20 into a patient. In addition, this continuous video image may enable a user to continuously view a procedure, e.g., a biopsy procedure performed by a biopsy forceps inserted through the instrument insertion port 30, so as to ensure that it proceeds safely and effectively.

The electronics control module 54 located on the handle 50 of the trans-nasal endoscope 10 may, in accordance with various embodiments, provide additional functionality that may be useful in a surgical procedure being performed thereby. FIG. 8. is a perspective view (with various components, such as the walls of the handle 50, being hidden so as not to obscure the features shown) of, among other components, the electronics control module 54, according to an embodiment. FIG. 8 illustrates the electronics control module 54 mounted on a control manifold 601. Specifically, mounted on the control manifold 601 are various buttons that allow a user to selectively control certain aspects of the image and/or video components of the trans-nasal endoscope 10. In an embodiment, the external video control unit 571 may include a menu of different video control functions, and the external video control unit 571 may be pre-programmed such that the buttons are mapped to pre-selected functions within that menu. For example, a first button may provide a first signal that is mapped to a first function from the menu of video control functions so that the external video control unit 571 causes the first function to be performed when the first button is pressed, and a second button may provide a second signal that is mapped to a second function from the menu of video control functions so that the external video control unit 571 causes the second function to be performed when the second button is pressed.

The menu of video control functions that may be provided by the external video control unit 571, and to which the first and second buttons may be mapped, may include any one or more of a white balancing function, an image capture function, a zoom function, a video capture start function, a video capture stop function, a brightness change function, a start video conference function, a change color spectrum function, a zoom picture function, a magnify picture function, a measure size of object function, a measure distance of object function, and a launch program or any other keyboard function on an external computer.

In the embodiment shown herein, the electronics control module 54 includes the white balance control button 541 as a first button, and the image capture control button 542 as the second button. The white balance control button 541 may be connected to the external video control unit 571 via the video display output cable 57. Upon a user pressing the white balance control button 541, a white balancing signal may be transmitted via the video display output cable 57 to the external video control unit 571, instructing the external video control unit 571 to perform, or cause to be performed by the video display device, a white balancing function on the image, e.g., a process used to adjust colors in an image to match the color of the light source so that white objects appear white.

The image capture control button 542 may also be connected to the external video control unit 571 via the video display output cable 57. Upon a user pressing the image capture control button 542, an image capture signal may be transmitted via the video display output cable 57 to the external video control unit 571, instructing the external video control unit 571 to perform, or cause to be performed by the video display device, an image capture function. The image capture function could include many different types of functions, e.g., capturing a specific single image frame for display and/or storage, capturing a specific time frame of images or video for display and/or storage, modifying an image or video signal so as to adjust any aspects thereof, etc.

Of course, it should be recognized that the electronic control module 54 may have configurations and/or control buttons that are different from those described herein, and that such different configurations and/or control buttons may be employed to control other aspects of an image or video system than described herein. It should also be recognized that certain aspects of the system may employ wireless connections, instead of the wired connections shown herein, to transmit signals and/or data related to the surgical procedure. For example, in embodiments, instead of the video display output cable 57, the trans-nasal endoscope 10 may employ wireless transmitters and receivers located in, e.g., the handle 50 and/or the external video control unit 571, transmit and receive the white balancing control signals and/or the image capture signals.

There are no limitations in terms of the particular embodiments described in this application, which are intended as illustrations of various aspects only. Many modifications and variations can be made without departing from its spirit and scope, as will be apparent to those skilled in the art.

Functionally equivalent methods and apparatuses, in addition to those enumerated herein, will be apparent to those skilled in the art from the foregoing descriptions. Such modifications and variations are intended to fall within the scope of the appended claims. Only the terms of the appended claims are intended to be limiting, along with the full scope of equivalents to which such claims are entitled. It is also to be understood that the terminology used herein, e.g., "and", "or", "including", "at least" as well as the use of plural or singular forms, etc., is for the purpose of describing examples of embodiments and is not intended to be limiting.

What is claimed is:

1. An endoscope suitably configured and sized for use in an unsedated trans-nasal endoscopy procedure, comprising:
a handle for gripping by a user, the handle including opposing roller knobs located on opposite sides of the handle and a rotatable thumb knob rotatable about the same axis about which the opposing roller knobs rotate;
a flexible shaft extending from the handle, the shaft having a generally constant outer diameter that is less than 4.5 mm and a working channel having a generally constant working channel diameter that is between 1.5 mm and 2.5 mm extending longitudinally therethrough, the shaft having a distal region that maintains the generally constant outer diameter and that is configured to be inserted into the nose of a patient and steered through the patient's nasal cavities in a left/right direction by the opposing roller knobs and in an up/down direction by the thumb knob via connection to a plurality of steering wires extending along the flexible shaft between the outer diameter of the flexible shaft and the working channel;
a circuit board located at the distal region of the shaft, the circuit board having a longitudinally-extending proximal portion and a distal leg that is bent radially inwardly about 90 degrees relative to the longitudinally-extending proximal portion of the circuit board; and
an illumination source mounted on the distal leg of the circuit board and radially outside the working channel so as not to impede the working channel such that the illumination source faces distally.

2. The endoscope of claim 1, further comprising:
a camera sensor mounted on the circuit board.

3. The endoscope of claim 2, wherein a distalmost face of the camera sensor and a distalmost face of the illumination source are located at the same longitudinal position of the endoscope shaft so as to be flush-mounted relative to a distalmost face of the shaft.

4. The endoscope of claim 3, wherein the distalmost face of the shaft is formed by a micro-molded tip component having an opening therein for the camera sensor and at least one pocket for receiving the illumination source.

5. The endoscope of claim 1, wherein the circuit board includes two distal legs that are angled radially inwardly perpendicular to the circuit board, and the illumination source includes an LED mounted on each leg.

6. The endoscope of claim 5, wherein the two LEDs and the camera sensor are positioned radially within the outer diameter of the shaft and radially outside the working channel so as not to impede the working channel.

7. The endoscope of claim 1, further comprising:
an electrical cable extending longitudinally through the shaft from the circuit board to the handle, the electrical cable being embedded between the outer diameter of the shaft and inner diameter of the working channel so as to extend parallel to the working channel.

8. The endoscope of claim 7, further comprising:
an electronic control module on the handle, the electronic control module connected to the electrical cable within the handle,
wherein the electronic control module includes at least one of a white balancing button and an image capture button.

9. The endoscope of claim 8, further comprising:
a video output cable extending from the handle; and
a video control unit connectable to the video output cable, the video control unit configured to receive a signal from the at least one of the white balancing button and the image capture button.

10. The endoscope of claim 9, further comprising:
a video display device connectable to the video control unit, wherein the video control unit is configured, upon receiving the signal from the at least one of the white balancing button and the image capture button, to control at least one corresponding aspect of a video display on the video display device.

11. An endoscope for use in a surgical procedure, comprising:
a handle for gripping by a user, the handle including opposing roller knobs and a rotatable thumb knob that rotate about a common lateral axis extending through the handle so as to provide one-handed operation of the knobs;
a shaft extending from the handle and configured to be inserted into and steered in at least four directions within a patient by the opposing roller knobs and the rotatable thumb knob, the shaft having an outer shaft wall with a diameter suitable for insertion into a patient's nasal cavity and a working channel disposed along a longitudinal axis of the shaft, the working channel defining a working channel wall, wherein the distance between the working channel wall and the outer shaft wall is maintained by a plurality of braided filaments to be 1 mm or less; and
a circuit board located in a distalmost region of the shaft, the circuit board having an imaging device mounted on a first portion thereof and having an illumination source mounted on a distal leg that is generally perpendicular to the longitudinal axis,
wherein the circuit board, imaging device and illumination source are situated in the 1 mm or less space between the working channel wall and the outer shaft wall such that the working channel extends along the longitudinal axis of the shaft in the distalmost region of the shaft.

12. The endoscope of claim 11, wherein the imaging device is a camera sensor mounted on the circuit board.

13. The endoscope of claim 12, wherein a distalmost face of the camera sensor and a distalmost face of the illumination source are located at the same longitudinal position of the endoscope shaft so as to be flush-mounted relative to a distalmost face of the shaft.

14. The endoscope of claim 13, wherein the distalmost face of the shaft is formed by a micro-molded tip component having an opening therein for the camera sensor and at least one pocket for receiving the illumination source.

15. The endoscope of claim 11, wherein the circuit board includes two distal legs that are angled radially inwardly perpendicular to the circuit board, and the illumination source includes a distal-facing LED mounted on each leg.

* * * * *